United States Patent [19]

Klar et al.

[11] Patent Number: 5,792,792
[45] Date of Patent: Aug. 11, 1998

[54] BORENOL DERIVATIVES, PROCESS FOR THEIR PRODUCTION AND THEIR PHARMACEUTICAL USE

[75] Inventors: Ulrich Klar; Hermann Graf; Günter Neef; Siegfried Blechert, all of Berlin, Germany

[73] Assignee: Schering Aktiengesellschaft, Berlin, Germany

[21] Appl. No.: 732,449

[22] PCT Filed: Apr. 13, 1995

[86] PCT No.: PCT/EP95/01341

§ 371 Date: Jan. 3, 1997

§ 102(e) Date: Jan. 3, 1997

[87] PCT Pub. No.: WO95/30650

PCT Pub. Date: Nov. 16, 1995

[30] Foreign Application Priority Data

May 5, 1994 [DE] Germany .................. 44 16 374.6

[51] Int. Cl.[6] ............... A61K 31/335; C07D 303/10
[52] U.S. Cl. ............... 514/475; 514/532; 514/539; 549/510; 549/553; 560/39; 424/450; 424/455
[58] Field of Search .................. 514/475, 532, 514/539; 549/510, 553; 560/39; 424/450, 455

[56] References Cited

U.S. PATENT DOCUMENTS 5,248,796  9/1993  Chen et al. ................ 549/510
5,405,972  4/1995  Holton et al. .............. 549/214

FOREIGN PATENT DOCUMENTS 253738  7/1987  European Pat. Off. .

OTHER PUBLICATIONS

Wender, P.A. et al, 'A New and Practical Approach to the Synthesis of Taxol and Taxol Analogues: The Pinene Path' J. Am. Chem. Soc. 1992, 114, pp. 5878–5879.

*Primary Examiner*—C. Warren Ivy
*Assistant Examiner*—Garth M. Dahlen
*Attorney, Agent, or Firm*—Millen, White, Zelano & Branigan, P.C.

[57] ABSTRACT

The invention relates to borneol derivatives of general formula I

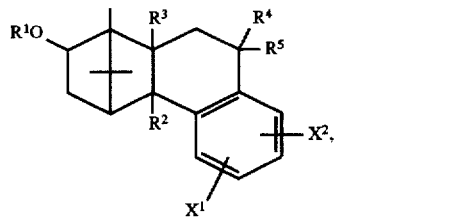

in which $R^1$ means $C(O)-CH(OR^6)-CH(NHR^7)-R^8$, $R^2$ means hydrogen, —OH, $C_1$–$C_{10}$ alkyl, $C_1$–$C_{10}$ alkoxy, —OC(O)$R^{9a}$, —OSO$_2$$R^{9a}$, —OP(O)(OH)$_2$, NHR$^{9a}$, NR$^{9a}$R$^{9b}$, $R^3$ means hydrogen, —OH, $C_1$–$C_{10}$ alkoxy, —OC(O)$R^{9b}$, —OSO$_2$$R^{9b}$, —OP(O)(OH)$_2$, or $R^2$, $R^3$ together mean an oxygen atom, $R^4$ means hydrogen, $C_1$–$C_{10}$ alkyl, —(CH$_2$)$_n$—OR$^{11a}$, $R^5$ means hydrogen, $C_1$–$C_{10}$ alkyl, —(CH$_2$)$_p$—OR$^{11b}$, or $R^4$, $R^5$ together mean an oxygen atom, a=CHR$^{10}$ group, n means 0 to 8, p means 1 to 8, $R^7$ means —C(O)$R^{12}$, —SO$_2$$R^{12}$, —C(O)OR$^{12}$, —C(O)NHR$^{9d}$, —C(O)NR$^{9d}$R$^{9e}$,

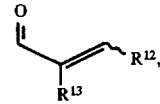

$R^8$ means aryl, $R^{9a-e}$, $R^{12}$ are the same or different and mean $C_1$–$C_{10}$ alkyl, $C_4$–$C_8$ cycloalkyl, aryl, $C_7$–$C_{16}$ aralkyl, $R^{10}$ means hydrogen, $C_1$–$C_{10}$ alkyl, —(CH$_2$)$_s$—OR$^{14}$, s means 1 to 8, $R^6$, $R^{11a,b}$, $R^{14}$ are the same or different and mean hydrogen, $C_1$–$C_{10}$ alkyl, aryl, $C_7$–$C_{16}$ aralkyl, —SO$_2$$R^{9c}$, —P(O)(OH)$_2$, $R^{13}$, $R^{15a,b}$ are the same or different and mean hydrogen, $C_1$–$C_{10}$ alkyl, aryl, $C_7$–$C_{16}$ aralkyl, $X^1$, $X^2$ are the same or different and mean X, X can be hydrogen, halogen, —OH, —NO$_2$, —N$_3$, —CN, —NR$^{15a}$R$^{15b}$, —NHSO$_2$R$^{15a}$, —CO$_2$R$^{15}$, $C_1$–$C_{10}$ alkyl, $C_1$–$C_{10}$ alkoxy, $C_1$–$C_{10}$ acyloxy, $C_1$–$C_{10}$ acyl, and, if $R^{15}$ means hydrogen, their salts with physiologically compatible bases, as well as the α-, β- or γ-cyclodextrin clathrates, as well as the compounds of formula I that are encapsulated with liposomes.

3 Claims, No Drawings

BORENOL DERIVATIVES, PROCESS FOR THEIR PRODUCTION AND THEIR PHARMACEUTICAL USE

This application is a 371 of PCT/EP95/01341, filed Apr. 13, 1995.

The invention relates to new pharmacologically active compounds, which have the power to influence tubulin polymerization or tubulin depolymerization.

A number of natural mitotic poisons are used as antitumor agents or are undergoing clinical trials. Various classes of these mitotic poisons exist that exert their cytotoxic effect either by inhibiting the polymerization of microtubuli in a spindle device (e.g., vinca alkaloids, colchicine) or accomplish this by a GTP-independent increase of the polymerization of the tubulin and prevention of the depolymerization of microtubuli (e.g., taxol, taxotere). Owing to previously little-understood physicochemical properties and the characteristics of neoplastic cells, mitotic poisons have a certain selectivity for tumor cells, but there is also significant cytotoxicity with regard to nontransformed cells.

Up until now, vinca alkaloids have had great importance in the combined chemotherapy of myeloid tumors. Taxanes have very recently opened up important applications that were not accessible by previously available cytostatic agents, e.g., ovarian cancers, malignant melanomas. The side-effects of taxanes are comparable to those of other cytostatic agents, however (e.g., loss of hair, sensory neuropathy). Multi-drug-resistant tumor cells, which overexpress the P-glycoprotein, are resistant to taxanes. The limited availability of the natural substance taxol also inhibits broader clinical trials.

Natural substances and synthetic pharmaceutical agents that have a spectrum of action unlike that of the previous mitotic poisons were therefore tested. An in vitro experimental arrangement makes it possible to search for substances that do not influence the GTP-dependent polymerization of tubulin, but influence the depolymerization of the microtubuli formed. Substances with such a profile of action should influence the versatile functions of microtubuli in extranuclear cell compartments less strongly than the dynamic of the spindle device during mitosis (metaphase, anaphase). Logically, such compounds should have fewer side-effects in vivo than taxanes or vinca alkaloids.

Tubulin is an essential component of the mitotic spindle. It is used, i.a., to preserve the cell shape, to transport organelles inside the cell, and to influence cell mobility.

Up until now, taxanes has represented the only known structural class that is able to accelerate the polymerization of tubulin (mainly in the G2 phase), as well as to stabilize the microtubuli polymers formed. This mechanism is clearly distinguishable from those that have other structural classes which also influence the phase-specific cell division. Thus, for example, substances from the group of vinca alkaloids (e.g., vincristines and vinblastines) but also colchicine inhibit the polymerization of the tubulin dimers in the M phase.

It has now been found that compounds of formula I that are comparatively simple to produce are able to inhibit the depolymerization of microtubuli without increasing the formation of microtubuli in a GTP-independent manner. Moreover, compounds with a completely new profile of action that are able to accelerate the depolymerization of microtubuli were identified. On the basis of these properties, the compounds of formula I represent valuable pharmaceutical agents that are basically able to supplement or replace taxanes, which are difficult to synthesize and which are still not available in sufficient quantity, such as, e.g., taxol and Taxotere®, in the treatment of malignant tumors (EP-A 253739).

The new borneol derivatives are characterized by general formula I

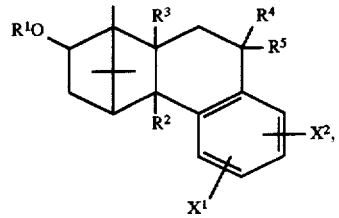

in which $R^1$ means $C(O)$—$CH(OR^6)$—$CH(NHR^7)$—$R^8$, $R^2$ means hydrogen, —OH, $C_1$–$C_{10}$ alkyl, $C_1$–$C_{10}$ alkoxy, —OC(O)$R^{9a}$, —OSO$_2R^{9a}$, —OP(O)(OH)$_2$, $NHR^{9a}$, $NR^{9a}R^{9b}$, $R^3$ means hydrogen, —OH, $C_1$–$C_{10}$ alkoxy, —OC(O)$R^{9b}$, —OSO$_2R^{9b}$, —OP(O)(OH)$_2$, or $R^2$, $R^3$ together mean an oxygen atom, $R^4$ means hydrogen, $C_1$–$C_{10}$ alkyl, —(CH$_2$)$_n$—OR$^{11a}$, $R^5$ means hydrogen, $C_1$–$C_{10}$ alkyl, —(CH$_2$)$_p$—OR$^{11b}$, or $R^4$, $R^5$ together mean an oxygen atom, a —CHR$^{10}$ group, n means 0 to 8, p means 1 to 8, $R^7$ means —C(O)$R^{12}$, —SO$_2R^{12}$, —C(O)OR$^{12}$, —C(O)NHR$^{9d}$, —C(O)NR$^{9d}R^{9e}$.

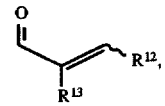

$R^8$ means aryl, $R^{9a-e}$, $R^{12}$ are the same or different and mean $C_1$–$C_{10}$ alkyl, $C_4$–$C_8$ cycloalkyl, aryl, $C_7$–$C_{16}$ aralkyl, $R^{10}$ means hydrogen, $C_1$–$C_{10}$ alkyl, —(CH$_2$)$_s$—OR$^{14}$, s means 1 to 8, $R^6$, $R^{11a,b}$, $R^{14}$ are the same or different and mean hydrogen, $C_1$–$C_{10}$ alkyl, aryl, $C_7$–$C_{16}$ aralkyl, —SO$_2R^{9c}$, —P(O)(OH)$_2$, $R^{13}$, $R^{15a,b}$ are the same or different and mean hydrogen, $C_1$–$C_{10}$ alkyl, aryl, $C_7$–$C_{16}$ aralkyl, $X^1$, $X^2$ are the same or different and mean X, X can be hydrogen, halogen, —OH, —NO$_2$, —N$_3$, —CN, —NR$^{15a}R^{15b}$, —NHSO$_2R^{15a}$, —CO$_2R^{15}$, $C_1$–$C_{10}$ alkyl, $C_1$–$C_{10}$ alkoxy, $C_1$–$C_{10}$ acyloxy, $C_1$–$C_{10}$ acyl, and, if $R^{15}$ means hydrogen, their salts with physiologically compatible bases, as well as their α-, β- or γ-cyclodextrin clathrates, as well as the compounds of general formula I that are encapsulated with liposomes.

The invention relates to the diastereomers and/or enantiomers of these borneol derivatives and also their mixtures.

As alkyl groups $R^2$, $R^4$, $R^5$, $R^6$, $R^{9a-e}$, $R^{10}$, $R^{11a,b}$, $R^{12}$, $R^{13}$, $R^{14}$, $R^{15a,b}$ and X, straight-chain or branched-chain alkyl groups with 1–10 carbon atoms can be considered, such as, for example, methyl, ethyl, propyl, isopropyl, butyl, isobutyl, tert-butyl, pentyl, isopentyl, neopentyl, heptyl, hexyl, decyl.

Alkyl groups $R^2$, $R^4$, $R^5$, $R^6$, $R^{9a-e}$, $R^{10}$, $R^{11a,b}$, $R^{12}$, $R^{13}$, $R^{14}$, $R^{15a,b}$ and X can be substituted by 1–3 halogen atoms, hydroxy groups, $C_1-C_4$ alkoxy groups, $C_6-C_{12}$ aryl groups, which can be substituted by 1–3 halogen atoms, di-$(C_1-C_4)$-alkylamines and tri-$(C_1-C_4)$ alkylammonium.

As cycloalkyl groups $R^{9a-e}$, $R^{12}$, substituted and unsubstituted radicals with 4 to 8 carbon atoms are suitable.

As aryl radical $R^6$, $R^8$, $R^{9a-e}$, $R^{10}$, $R^{11a,b}$, $R^{12}$, $R^{13}$, $R^{14}$, $R^{15a,b}$, substituted and unsubstituted carbocyclic or heterocyclic radicals, such as, e.g., phenyl, naphthyl, furyl, thienyl, pyridyl, pyrazolyl, pyrimidinyl, oxazolyl, pyridazinyl, pyrazinyl, quinolyl, which can be substituted several times by the groups that are defined in X, are suitable.

The alkoxy, acyl and acyloxy groups that are contained in $R^2$, $R^3$ and X of general formula I are to contain 1 to 10 carbon atoms in each case, whereby methoxy, ethoxy, propoxy, isopropoxy, t-butyloxy, formyl, acetyl, propionyl and isopropionyl groups are preferred.

The $C_7-C_{16}$ aralkyl groups in $R^6$, $R^{9a-e}$, $R^{11a,b}$, $R^{12}$, $R^{13}$, $R^{14}$, $R^{15a,b}$ can contain up to 14 C atoms, preferably 6 to 10 C atoms, in the ring and 1 to 4 atoms, preferably 1 to 2 atoms, in the alkyl chain. Preferred aralkyl radicals are, e.g., benzyl, phenylethyl, naphthylmethyl or naphthylethyl. The rings can be substituted several times by the groups that are defined in X.

Free hydroxy groups in $R^1$, $R^2$, $R^3$, $R^4$, $R^5$, $R^{10}$ and X can be modified functionally, for example by etherification or esterification, whereby free hydroxy groups are preferred.

As ether and acyl radicals, the radicals that are known to one skilled in the art are suitable. Preferred are easily cleavable ether radicals, such as, for example, the tetrahydropyranyl, tetrahydrofuranyl, tert-butyldimethylsilyl, tert-butyldiphenylsilyl, tribenzylsilyl radical. As acyl radicals, e.g., acetyl, propionyl, butyryl, benzoyl are suitable.

Halogen in the definitions for X means fluorine, chlorine, bromine and iodine.

For salt formation with the free acids ($R^{15}=H$), inorganic and organic bases are suitable, as they are known to one skilled in the art for the formation of physiologically compatible salts. For example, there can be mentioned: alkali hydroxides, such as sodium or potassium hydroxide, alkaline-earth hydroxides, such as calcium hydroxide, ammonia, amines, such as ethanolamine, diethanolamine, triethanolamine, N-methylglucamine, morpholine, tris-(hydroxymethyl)-methylamine, etc.

The invention also relates to a process for the production of borneol derivatives of formula I, which is characterized in that an olefin of general formula II

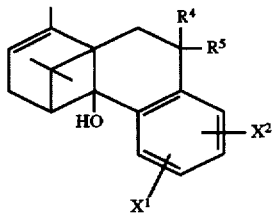

in which $R^4$, $R^5$, $X^1$ and $X^2$ have the above-mentioned meanings and are optionally protected in hydroxyl groups that contain $X^1$ or $X^2$, is epoxidated, and the epoxide formed is rearranged without isolation into an alcohol, of general formula III

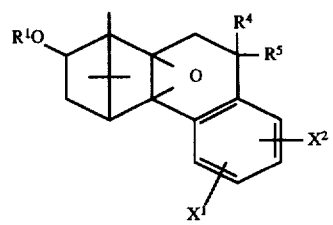

in which $R^4$, $R^5$, $X^1$ and $X^2$ have the above-mentioned meanings and hydroxyl groups that are contained in $R^1$, $X^1$ or $X^2$ are optionally protected, and this rearranged product is converted to a derivative of general formula I.

The reaction conditions of the above-named process stages are:

a) II→III

The epoxidation of the double bond is carried out with a peroxy compound, such as, e.g., meta-chloroperbenzoic acid, peroxotrifluoroacetic acid, hydrogen peroxide, tert-butyl hydroperoxide optionally with the addition of a Lewis acid, such as, e.g., titanium tetraisopropoxide in an inert solvent, such as, e.g., dichloromethane, toluene at –40° C. to +40° C. The reaction with tert-butyl hydroperoxide and titanium tetraisopropoxide in toluene at –10° C. to +25° C. is preferred.

The rearrangement of the epoxide formed is catalyzed by acids, such as, e.g., para-toluenesulfonic acid, silica gel, acid ion exchanger resins, hydrochloric acid. The use of silica gel is preferred.

b) III→I

The conversion of compounds of formula III to a compound of formula I can be carried out in various sequences:

1) Esterification of the alcohol function ($R^1$=hydrogen) modification of $R^4$ and/or $R^5$→optionally epoxide opening, if $R^2$ and $R^3$ together represent an oxygen atom, optionally with subsequent modification of $R^2$ and $R^3$.

2) Esterification of alcohol function ($R^1$=hydrogen) →optionally epoxide opening, if $R^2$ and $R^3$ together represent an oxygen atom, optionally with subsequent modification of $R^2$ and $R^3$ →modification of $R^4$ and/or $R^5$.

3) Protection of alcohol function ($R^1$=hydrogen) →optionally epoxide opening, if $R^2$ and $R^3$ together represent an oxygen atom, optionally with subsequent modification of $R^2$ and $R^3$→modification of $R^4$ and/or $R^5$→release and subsequent esterification of alcohol function ($R^1$=hydrogen).

4) Protection of alcohol function ($R^1$=hydrogen) →modification of $R^4$ and/or $R^5$→release and subsequent esterification of the alcohol function ($R^1$=hydrogen)→optionally epoxide opening, if $R^2$ and $R^3$ together represent an oxygen atom, optionally with subsequent modification of $R^2$ and $R^3$.

For esterification of the alcohol function ($R^1$=hydrogen), 1,4-diazabicyclo[2.2.2]octane (DABCO) is deprotonated with a base, such as, e.g., metal hydrides (e.g., sodium hydride), alkali alcoholates (e.g., sodium methanolate, potassium-tert-butanolate), alkali hexamethyl disilazane (e.g., sodium hexamethyl disilazane), 1,5diazabicyclo[4.3.0] non-5-ene (DBN), 1,8-diazabicyclo[5.4.0]undec-7-ene (DBU), triethylamine, 4-(dimethylamino)pyridine (DMAP) and reacted with suitable carboxylic acid derivatives, such as, e.g., acid amides, acid halides, acid anhydrides in an inert solvent, such as, e.g., dichloromethane, diethyl ether, tetrahydrofuran at –70° C. to +50° C. Preferred is the reaction with sodium hexamethyl disilazane as a base, a cyclic acid amide as a carboxylic acid derivative, tetrahydrofuran as a solvent at temperatures of −40° C. to +25° C.

If $R^4$ and $R^5$ together represent a =$CHR^{10}$ group, the functionalization of the olefinic double bond can be carried out according to the methods that are known to one skilled in the art. For example, hydrogen can be stored, e.g., by catalyzed hydrogenation, hydroxyl groups can be introduced by water addition (hydroboration, oxymercurization) or by 1,2-bis-hydroxylation, e.g., with osmium tetroxide or potassium permanganate. The introduction of a carbonyl group ($R^4$, $R^5$ together represent an oxygen atom) is possible after cleavage of the double bond, e.g., by ozonolysis or by oxidative cleavage of a 1,2-diol. A carbonyl group that is produced in such a way can be used, for example, reduced, alkylated or as a carbonyl component in a Wittig reaction in building modified =$CHR^{10}$ groups.

If $R^2$ and $R^3$ together represent an oxygen atom, the epoxide can be reacted by nucleophiles, such as, for example, water, carboxylic acid derivatives (carboxylic acids, carboxylic acid halides, carboxylic anhydrides), sulfonic acid derivatives (sulfonic acids, sulfonic acid halides, sulfonic anhydrides), amines, in the presence of mineral or organic acids, such as, for example, hydrochloric acid, para-toluenesulfonic acid or Lewis acids, such as, for example, boron trifluoride etherate, titanium tetraisopropoxide, cerium ammonium nitrate either in inert solvents or solvents that act as nucleophiles at −70° C. up to +50° C.

Biological Effects and Applications of New Borneol Derivatives:

The new compounds of formula I are valuable pharmaceutical agents. They interact with tubulin by stabilizing the microtubuli formed and are thus able to influence cell division in a phase-specific manner. This relates mainly to quick-growing, neoplastic cells, whose growth is largely unaffected by intercellular regulating mechanisms. Active ingredients of this type are mainly suitable for treating malignant tumors. As applications, for example, the treatment of ovarian, stomach, colon, adeno-, breast, lung, head and neck carcinomas, malignant melanoma, acute lymphocytic and myelocytic leukemia can be mentioned. The compounds according to the invention can be used by themselves or to achieve additive or synergistic effects in combination with other principles and classes of substances that can be used in tumor therapy.

As examples, there can be mentioned the combination with

Platinum complexes such as, e.g., cis-platinum, carboplatinum, intercalating substances, e.g., from the class of anthracyclins, such as, e.g., doxorubicin or from the class of anthrapyrazoles, such as, e.g., CI-941, substances that interact with tubulin, e.g., from the class of vinca alkaloids, such as, e.g., vincristine, vinblastine or from the class of taxanes, such as, e.g., taxol, taxotere or from the class of macrolides, such as, e.g., rhizoxin or other compounds, such as, e.g., colchicine, combretastatin A-4, DNA topoisomerase inhibitors, such as, e.g., camptothecin, etoposide, topotecan, teniposide, folate- or pyrimidine-antimetabolites, such as, e.g., lometrexol, gemcitubin, compounds that alkylate DNA, such as, e.g., adozelesin, dystamycin A, inhibitors of growth factors (e.g., of PDGF, EGF, TGFβ, EGF), such as, e.g., somatostatin, suramin, bombesin antagonists, inhibitors of protein tyrosine kinase or protein kinases A or C, such as, e.g., erbstatin, genisteine, staurosporine, ilmofosine, 8-Cl-cAMP, antihormones from the class of antigestagens, such as, e.g., mifepristone, onapristone, or from the class of antiestrogens, such as, e.g., tamoxifen, or from the class of antiandrogens, such as, e.g., cyproterone acetate, compounds that inhibit metastases, e.g., from the class of eicosanoids, such as, e.g., $PGI_2$, $PGE_1$, 6-oxo-$PGE_1$ as well as their more stable derivatives (e.g., iloprost, cicaprost).

The invention also relates to pharmaceutical agents that are based on pharmaceutically compatible compounds, i.e., compounds that are not toxic in the doses used, of general formula I, optionally together with the adjuvants and vehicles that are commonly used.

The compounds according to the invention can be worked into pharmaceutical preparations for enteral, percutaneous, parenteral or local administration according to methods of galenicals that are known in the art. They can be administered in the form of tablets, coated tablets, gel capsules, granulates, suppositories, implants, injectable sterile aqueous or oily solutions, suspensions or emulsions, ointments, creams and gels.

In this case, the active ingredient or active ingredients can be mixed with the adjuvants that are commonly used in galenicals, such as, e.g., gum arabic, talc, starch, mannitol, methyl cellulose, lactose, surfactants such as Tweens or Myrj, magnesium stearate, aqueous or non-aqueous vehicles, paraffin derivatives, wetting agents, dispersing agents, emulsifiers, preservatives and flavoring substances for taste correction (e.g., ethereal oils).

The invention thus also relates to pharmaceutical compositions, which as active ingredient contain at least one compound according to the invention. A dosage unit contains about 0.1–100 mg of active ingredient(s). In humans, the dosage of the compounds according to the invention is approximately 0.1–1000 mg per day.

The embodiments below are used to explain the process according to the invention in more detail.

EXAMPLE 1

[1R-[1α,2β(2R*,3S*),4α,4aβ,10aβ]]-3-[[(1,1-Dimethylethoxy)carbonyl]amino]-2-hydroxybenzenepropanoic acid-9-methylene-1,2,3,4,4a,9,10,10a-octahydro-1,12,12-trimethyl-4a,10a-epoxy-1,4-methanophenanthren-2-ylester 150 mg (214 μmol) of polar compound A that is presented according to Example 1a is dissolved under an atmosphere of dry argon in 7 ml of anhydrous tetrahydrofuran, mixed with 0.29 ml of a 1.1M solution of tetrabutylammonium fluoride in tetrahydrofuran and stirred for 1 hour at 23° C. It is concentrated by evaporation, and the residue is purified by chromatography on about 40 ml of fine silica gel with a gradient system that consists of n-hexane and ethyl acetate. 113 mg (207 μmol, 97%) of the title compound is isolated as colorless foam.

$^1$H-NMR (DMSO-d6, 80° C.): δ=0.78 (3H), 0.91 (3H), 1.02 (3H), 1.32 (9H), 1.58 (1H), 2.17 (1H), 2.75 (2H), 3.08 (1H), 4.36 (1H), 4.93 (1H), 5.01 (1H), 5.07 (1H), 5.33 (1H), 5.49 (1H), 6.53 (1H), 7.20–7.38 (7H), 7.56 (2H) ppm.

EXAMPLE 1a

[1R-[1α,2β(2R*,3S*),4α,4aβ,10aβ]]-3-[[(1,1-Dimethylethoxy)carbonyl]amino]-2-(triisopropylsilyloxy)

benzenepropanoic acid-9-methylene-1,2,3,4,4a,9,10,10a-octahydro-1,12,12-trimethyl-4a,10a-epoxy-1,4-methanophenanthren-2-ylester (A) and [1S-[1α,2β(2R*,3S*),4α,4aβ,10aβ]]-3-[[1,1-dimethylethoxy)carbonyl]amino]-2-(triisopropylsilyloxy)benzenepropanoic acid-9-methylene-1,2,3,4,4a,9,10,10a-octahydro-1,12,12-trimethyl-4a,10a-epoxy-1,4-methanophenanthren-2-ylester (B)

79 mg (280 μmol) of the mixture that is presented according to Example 1b as well as 176 mg of the β-lactam that is presented according to Example 1c are dissolved under an atmosphere of dry argon in 30 ml of anhydrous tetrahydrofuran, mixed at −35° C. with 0.34 ml of a 1M solution of sodium hexamethyl disilazane in tetrahydrofuran and stirred for 15 more minutes. It is poured into saturated ammonium chloride solution, extracted several times with ethyl acetate, the combined organic extracts are washed with water and saturated sodium chloride solution and dried on sodium sulfate. The residue that is obtained after filtration and removal of solvent is separated by chromatography on about 70 ml of fine silica gel with a gradient system that consists of n-hexane and ethyl acetate. 26 mg (37 μmol, 13%) of title compound B is isolated as a nonpolar component, and 91 mg (130 μmol, 46%) of title compound A is isolated as a polar component, in each case as colorless foam.

$^1$H-NMR (CDCl$_3$) of A: δ=0.8–1.47 (39H), 1.71 (1H), 2.22 (1H), 2.64 (1H), 2.71 (1H), 3.03 (1H), 4.66 (1H), 4.96 (1H), 5.02 (1H), 5.16 (1H), 5.47 (1H), 5.92 (1H), 7.16–7.54 (9H) ppm.

$^1$H-NMR (CDCl$_3$) of B: δ=0.8–1.47 (39H), 1.79 (1H), 2.38 (1H), 2.68 (1H), 2.70 (1H), 3.15 (1H), 4.69 (1H), 5.06 (1H), 5.08 (1H), 5.22 (1H), 5.50 (1H), 5.71 (1H), 7.18–7.56 (9H) ppm.

EXAMPLE 1b
[1R-(1α,2β,4α,4aβ,10aβ)]-9-Methylene-1,2,3,4,4a,9,10,10a-octahydro-1,12,12-trimethyl-4a,10a-epoxy-1,4-methanophenanthren-2-ol (A) and [1S-(1α,2β,4α,4aβ,10aβ)]-9-methylene-1,2,3,4,4a,9,10,10a-octahydro-1,12,12-trimethyl-4a,10a-epoxy-1,4-methanophenanthren-2-ol (B)

2.1 g (7.88 mmol) of an approximately 7:3 mixture of [4R-(4α,4aβ10aα)]-9-methylene-3,4,4a,9,10,10a-hexahydro-1,11,11-trimethyl-4,10a-methanophenanthren-4a-ol and [4S-(4α,4aβ,10aα)]-9-methylene-3,4,4a,9,10,10a-hexahydro-1,11,11-trimethyl-4,10a-methanophenanthren-4a-ol, which has been produced analogously to the process described on page 5879 in J. Am. Chem. Soc. 1992, is dissolved under an atmosphere of dry argon in 80 ml of anhydrous dichloromethane, and it is cooled to 0° C. It is mixed with 2.4 ml of titanium(IV) isopropylate, 1.5 ml of a 6.5M anhydrous solution of tert-butyl hydroperoxide in toluene and stirred for 0.5 hour. It is poured into water, extracted several times with diethyl ether, the combined organic extracts are washed with water and saturated sodium chloride solution and dried on sodium sulfate. The residue that is obtained after filtration and removal of solvent is separated by chromatography on about 200 ml of fine silica gel with a gradient system that consists of n-hexane and ethyl acetate. 1.39 g (4.92 mmol, 62%) of title compounds A and B is isolated as crystalline solid. By crystallization from diisopropyl ether, isomer A that is contained in excess in the product mixture can be obtained.

$^1$H-NMR (CDCl$_3$): δ=0.79 (3H), 0.88 (3H), 1.11 (3H), 1.58 (1H), 2.38 (1H), 2.68 (1H), 2.74 (1H), 3.08 (1H), 3.79 (1H), 3.97 (1H), 5.02 (1H), 5.48 (1H), 7.30 (2H), 7.51 (2H) ppm.

EXAMPLE 1c
(3R,4S)-1-[(1,1-Dimethylethoxy)carbonyl]-3-triisopropylsilyloxy-4-phenyl-2-azetidinone 2.5 g (7.82 mmol) of (3R,4S)-3-triisopropylsilyloxy-4-phenylazetidin-2-one, which has been produced analogously to the process described in Tetrahedron 48, 6985 (1992), is dissolved under an atmosphere of dry argon in 50 ml of anhydrous dichloromethane, cooled to 0° C., mixed with 3.1 ml of triethylamine, 3.65 ml of pyrocarbonic acid-di-tert-butyl ether as well as a catalytic amount of dimethylaminopyridine. It is allowed to heat to 23° C. and to stir for 16 hours. It is poured into saturated ammonium chloride solution, extracted several times with diethyl ether, the combined organic extracts are washed with water and saturated sodium chloride solution and dried on sodium sulfate. The residue that is obtained after filtration and removal of solvent is separated by chromatography on about 300 ml of fine silica gel with a gradient system that consists of n-hexane and ethyl acetate. 3.1 g (7.39 mmol, 94%) of the title compound is isolated as crystalline solid.

$^1$H-NMR (CDCl$_3$): δ=0.80–1.02 (21H), 1.40 (9H), 5.07 (1H), 5.17 (1H), 7.27–7.40 (5H) ppm.

EXAMPLE 1d
(3R,4S)-1-Benzoyl-3-triisopropylsilyloxy-4-phenyl-2-azetidinone 5.0 g (15.6 mmol) of (3R,4S)-3-triisopropylsilyloxy-4-phenylazetidin-2-one, which has been produced analogously to the process described in Tetrahedron 48, 6985 (1992), is dissolved under an atmosphere of dry argon in 100 ml of anhydrous dichloromethane, cooled to 0° C., mixed with 6.2 ml of triethylamine, 3.85 ml of benzoyl chloride as well as a catalytic amount of dimethylaminopyridine. It is allowed to heat to 23° C. and to stir for 16 hours. It is poured into saturated ammonium chloride solution, extracted several times with diethyl ether, the combined organic extracts are washed with water and saturated sodium chloride solution and dried on sodium sulfate. The residue that is obtained after filtration and removal of solvent is separated by chromatography on about 400 ml of fine silica gel with a gradient system that consists of n-hexane and ethyl acetate. 6.43 g (15.2 mmol, 97%) of the title compound is isolated as crystalline solid.

$^1$H-NMR (CDCl$_3$): δ=0.80–1.07 (21H), 5.25 (1H), 5.43 (1H), 7.27–7.43 (5H), 7.48 (2H), 7.59 (1H), 8.03 (2H) ppm.

EXAMPLE 1e
(3R,4S)-1-Cyclohexylcarbonyl-3-triisopropylsilyloxy-4-phenyl-2-azetidinone 2.0 g (6.3 mmol) of (3R,4S)-3-triisopropylsilyloxy-4-phenylazetidin-2-one, which has been produced analogously to the process described in Tetrahedron 48, 6985 (1992), is reacted analogously to Example 1d with use of cyclohexanecarboxylic acid chloride and, after working-up and purification, 2.6 g (6.1 mmol, 96%) of the title compound is isolated.

$^1$H-NMR (CDCl$_3$): δ=0.81–1.03 (21H), 1.12–2.04 (10H), 3.03 (1H), 5.14 (1H), 5.19 (1H), 7.18–7.37 (5H) ppm.

EXAMPLE 1f
(3R,4S)-1-Acetyl-3-triisopropylsilyloxy-4-phenyl-2-azetidinone 2.0 g (6.3 mmol) of (3R,4S)-3-triisopropylsilyloxy-4-phenylazetidin-2-one, which has been produced analogously to the process described in Tetrahedron 48, 6985 (1992), is reacted analogously to Example 1d with use of acetyl chloride and, after working-up and purification, 1.8 g (5.0 mmol, 79%) of the title compound is isolated.

¹H-NMR (CDCl₃): δ=0.77–1.04 (21H), 2.45 (3H), 5.17 (1H), 5.22 (1H), 7.20–7.39 (5H) ppm.

EXAMPLE 2

[1S-[1α,2β(2R*,3S*),4α,4aβ,10aβ]]-3-[[(1,1-Dimethylethoxy)carbonyl]amino]-2-hydroxybenzenepropanoic acid-9-methylene-1,2,3,4,4a,9,10,10a-octahydro-1,12,12-trimethyl-4a,10a-epoxy-1,4-methanophenanthren-2-ylester Analogously to Example 1, 26 mg (37 μmol) of nonpolar compound B that is presented according to Example 1a is reacted. After working-up and purification, 14 mg (25 μmol, 69%) of the title compound is obtained as colorless foam.

¹H-NMR (CDCl₃): δ=0.84 (3H), 0.96 (3H), 1.08 (3H), 1.42 (9H), 1.83 (1H), 2.40 (1H), 2.70 (1H), 2.72 (1H), 3.18 (1H), 3.21 (1H), 4.58 (1H), 5.02 (1H), 5.10 (1H), 5.28 (1H), 5.50 (1H), 5.55 (1H), 7.22–7.38 (9H) ppm.

EXAMPLE 3

[1R-[1α,2β(2R*,3S*),4α,4aβ,10aβ]]-3-[Benzoylamino]-2-hydroxybenzenepropanoic acid-9-methylene-1,2,3,4,4a,9,10,10a-octahydro-1,12,12-trimethyl-4a,10a-epoxy-1,4-methanophenanthren-2-ylester 100 mg (142 μmol) of polar compound A that is presented according to Example 3a is reacted analogously to Example 1 and, after working-up and purification, 66 mg (120 μmol/85%) of the title compound is isolated as colorless foam.

¹H-NMR (CDCl₃): δ=0.82 (3H), 0.91 (3H), 0.98 (3H), 1.81 (1H), 2.29 (1H), 2.68 (1H), 2.71 (1H), 2.91 (1H), 3.59 (1H), 4.71 (1H), 4.88 (1H), 5.13 (1H), 5.40 (1H), 5.71 (1H), 7.18 (2H), 7.22–7.40 (6H), 7.40–7.59 (4H), 7.70 (1H), 7.87 (2H) ppm.

EXAMPLE 3a

[1R-[1α,2β(2R*,3S*),4α,4aβ,10aβ]]-3-[Benzoylamino]-2-(triisopropylsilyloxy)benzenepropanoic acid-9-methylene-1,2,3,4,4a,9,10,10a-octahydro-1,12,12-trimethyl-4a,10a-epoxy-1,4-methanophenanthren-2-ylester (A) and [1S-[1α,2β(2R*,3S*),4α,4aβ,10aβ]]-3-[benzoylamino]-2-(triisopropylsilyloxy)benzenepropanoic acid-9-methylene-1,2,3,4,4a,9,10,10a-octahydro-1,12,12-trimethyl-4a,10a-epoxy-1,4-methanophenanthren-2-ylester (B)

80 mg (283 μmol) of the mixture that is presented according to Example 1b as well as 181 mg of the β-lactam that is presented according to Example 1d are reacted analogously to Example 1a and, after working-up and purification, 24 mg (34 μmol, 12%) of title compound B as a nonpolar component as well as 100 mg (142 μmol, 50%) of title compound A as polar component are isolated respectively as colorless foam.

¹H-NMR (CDCl₃) of A: δ=0.8–1.22 (30H), 1.72 (1H), 2.20 (1H), 2.64 (1H), 2.66 (1H), 2.95 (1H), 4.78 (1H), 4.92 (1H), 5.05 (1H), 5.42 (1H), 5.68 (1H), 7.17–7.58 (12H), 7.65 (1H), 7.92 (2H) ppm.

¹H-NMR (CDCl₃) of B: δ=0.77 (3H), 0.80 (3H), 0.85–1.18 (24H), 1.65 (1H), 2.28 (1H), 2.53 (1H), 2.61 (1H), 2.79 (1H), 4.78 (1H), 5.02 (1H), 5.15 (1H), 5.46 (1H), 5.78 (1H), 7.11 (2H), 7.21–7.57 (10H), 7.74 (1H), 7.92 (2H) ppm.

EXAMPLE 4

[1S-[1α,2β(2R*,3S*),4α,4aβ,10aβ]]-3-[Benzoylamino]-2-hydroxybenzenepropanoic acid-9-methylene-1,2,3,4,4a,9,10,10a-octahydro-1,12,12-trimethyl-4a,10a-epoxy-1,4-methanophenanthren-2-ylester 24 mg (34 μmol) of nonpolar compound B that is presented according to Example 3a is reacted analogously to Example 1 and, after working-up and purification, 10 mg (18 μmol, 54%) of the title compound is isolated as colorless foam.

¹H-NMR (CDCl₃): δ=0.81 (3H), 0.90 (6H), 1.76 (1H), 2.32 (1H), 2.63 (1H), 2.67 (1H), 3.00 (1H), 3.34 (1H), 4.69 (1H), 5.07 (1H), 5.12 (1H), 5.47 (1H), 5.90 (1H), 7.16–7.58 (13H), 7.87 (2H) ppm.

EXAMPLE 5

[1S-[1α,2β(2R*,3S*),4α,4aβ,10aβ]]-3-[[(1,1-Dimethylethoxy)carbonyl]amino]-2-hydroxybenzenepropanoic acid-9-methylene-1,2,3,4,4a,9,10,10a-octahydro-1,11,11-trimethyl-4a-methoxy-10a-hydroxy-1,4-methanophenanthren-2-ylester 22 mg (30 μmol) of the compound that is presented according to Example 5a is reacted analogously to Example 1 and, after working-up and purification, 9 mg (16 μmol, 52%) of the title compound is isolated as colorless foam.

¹H-NMR (CDCl₃): δ=0.65 (3H), 1.01 (6H), 1.43 (9H), 2.07 (1H), 2.41 (1H), 2.57 (1H), 2.73 (2H), 2.82 (3H), 3.27 (1H), 3.82 (1H), 4.51 (1H), 5.12 (1H), 5.21 (2H), 5.33 (1H), 6.23 (1H), 7.22–7.50 (9H) ppm.

EXAMPLE 5a

[1S-[1α,2β(2R*,3S*),4α,4aβ,10aβ]]-3-[[(1,1-Dimethylethoxy)carbonyl]amino]-2-(triisopropylsilyloxy)benzenepropanoic acid-9-methylene-1,2,3,4,4a,9,10,10a-octahydro-1,11,11-trimethyl-4a-methoxy-10a-hydroxy-1,4-methanophenanthren-2-ylester 20 mg (28 μmol) of nonpolar compound B that is presented according to Example 1a is dissolved in a mixture of 0.2 ml of dichloromethane and 2 ml of methanol, mixed with 200 mg of DOWEX 50 WX 4 and stirred under an atmosphere of dry argon for 5 hours at 23° C. It is filtered, the filtrate is washed with saturated sodium bicarbonate solution, saturated sodium chloride solution and dried on magnesium sulfate. After filtration and removal of solvent, 12 mg (16 μmol, 57%) of the title compound is isolated as colorless foam, which is further reacted without purification.

¹H-NMR (CDCl₃): δ=0.64 (3H), 0.80–1.09 (27H), 1.44 (9H), 2.09 (1H), 2.43 (1H), 2.57 (1H), 2.68 (1H), 2.75 (1H), 2.80 (3H), 3.70 (1H), 4.60 (1H), 5.10 (1H), 5.12 (1H), 5.20 (1H), 5.34 (1H), 6.08 (1H), 7.17–7.49 (9H) ppm.

EXAMPLE 6

[1R-[1α,2β(2R*,3S*),4α,4aβ,10aβ]]-3-[[(1,1-Dimethylethoxy)carbonyl]amino]-2-hydroxybenzenepropanoic acid-9-methylene-1,2,3,4,4a,9,10,10a-octahydro-1,11,11-trimethyl-4a-methoxy-10a-hydroxy-1,4-methanophenanthren-2-ylester 15.6 mg (21 μmol) of the compound that is presented according to Example 6a is reacted analogously to Example 1 and, after working-up and purification, 8.6 mg (15 μmol, 71%) of the title compound is isolated as colorless foam.

¹H-NMR (CDCl₃): δ=0.65 (3H), 1.01 (6H), 1.43 (9H), 2.17 (1H), 2.38 (1H), 2.58 (1H), 2.73 (2H), 2.86 (3H), 3.11 (1H), 3.92 (1H), 4.56 (1H), 5.11 (1H), 5.21 (2H), 5.35 (1H), 6.21 (1H), 7.20–7.50 (9H) ppm.

EXAMPLE 6a

[1R-[1α,2β(2R*,3S*),4α,4aβ,10aβ]]-3-[[(1,1-Dimethylethoxy)carbonyl]amino]-2-(triisopropylsilyloxy)benzenepropanoic acid-9-methylene-1,2,3,4,4a,9,10,10a-octahydro-1,11,11-trimethyl-4a-methoxy-10a-hydroxy-1,4-methanophenanthren-2-ylester 15 mg (21 μmol) of polar compound A that is presented according to Example 1a is reacted analogously to Example 5a and, after working-up, 15.7 mg (21 µmol, 100%) of the title compound is isolated as colorless foam, which is further reacted without purification.

$^1$H-NMR (CDCl$_3$): δ=0.63 (3H), 0.78–1.04 (27H), 1.43 (9H), 2.03 (1H), 2.30 (1H), 2.58 (1H), 2.68 (1H), 2.74 (1H), 2.80 (3H), 3.82 (1H), 4.69 (1H), 5.11 (1H), 5.14 (1H), 5.27 (1H), 5.34 (1H), 6.39 (1H), 7.16–7.48 (9H) ppm.

EXAMPLE 7

[1R-[1α,2β(2R*,3S*),4α,4aβ,10aβ]]-3-[[(1,1-Dimethylethoxy)carbonyl]amino]-2-hydroxybenzenepropanoic acid-9-methylene-1,2,3,4,4a,9,10,10a-octahydro-1,11,11-trimethyl-4a-ethoxy-10a-hydroxy-1,4-methanophenanthren-2-ylester 16 mg (21 µmol) of the compound that is presented according to Example 7a is reacted analogously to Example 1 and, after working-up and purification, 7.8 mg (13 µmol, 63%) of the title compound is isolated as colorless foam.

$^1$H-NMR (CDCl$_3$): δ=0.64 (3H), 1.01 (6H), 1.06 (3H), 1.41 (9H), 2.22–2.43 (2H), 2.58 (1H), 2.68–2.90 (3H), 2.93–3.13 (2H), 4.04 (1H), 4.56 (1H), 5.12 (1H), 5.18 (1H), 5.32 (2H), 6.36 (1H), 7.18–7.50 (9H) ppm.

EXAMPLE 7a

[1R-[1α,2β(2R*,3S*),4α,4aβ,10aβ]]-3-[[(1,1-Dimethylethoxy)carbonyl]amino]-2-(triisopropylsilyloxy)benzenepropanoic acid-9-methylene-1,2,3,4,4a,9,10,10a-octahydro-1,11,11-trimethyl-4a-ethoxy-10a-hydroxy-1,4-methanophenanthren-2-ylester 15 mg (21 µmol) of polar compound A that is presented according to Example 1a is reacted analogously to Example 5a with use of ethanol and, after working-up, 16 mg (21 µmol, 100%) of the title compound, which is further reacted without purification, is isolated as colorless foam.

$^1$H-NMR (CDCl$_3$): δ=0.63 (3H), 0.78–1.12 (30H), 1.43 (9H), 2.13–2.37 (2H), 2.57 (1H), 2.64–2.86 (3H), 3.08 (1H), 3.98 (1H), 4.69 (1H), 5.12 (2H), 5.33 (2H), 6.33 (1H), 7.15–7.48 (9H) ppm.

EXAMPLE 8

[1S-[1α,2β(2R*,3S*),4α,4aβ,10aβ]]-3-[[(1,1-Dimethylethoxy)carbonyl]amino]-2-hydroxybenzenepropanoic acid-9-methylene-1,2,3,4,4a,9,10,10a-octahydro-1,11,11-trimethyl-4a,10a-dihydroxy-1,4-methanophenanthren-2-ylester 6.5 mg (9.0 µmol) of the compound that is presented according to Example 8a is reacted analogously to Example 1 and after working-up and purification, 3.5 mg (6.2 µmol, 69%) of the title compound is isolated as colorless foam.

1H-NMR (CDCl$_3$): δ=0.69 (3H), 1.01 (3H), 1.07 (3H), 1.48 (9H), 2.26–2.49 (2H), 2.54 (1H), 2.76 (1H), 2.88 (1H), 3.25 (1H), 4.40 (1H), 4.54 (1H), 4.84 (1H), 5.08 (1H), 5.34 (1H), 5.37 (1H), 5.53 (1H), 5.65 (1H), 7.20–7.49 (9H) ppm.

EXAMPLE 8a

[1S-[1α,2β(2R*,3S*),4α,4aβ,10aβ]]-3-[[(1,1-Dimethylethoxy)carbonyl]amino]-2-(triisopropylsilyloxy)benzenepropanoic acid-9-methylene-1,2,3,4,4a,9,10,10a-octahydro-1,11,11-trimethyl-4a,10a-dihydroxy-1,4-methanophenanthren-2-ylester 14 mg (20 µmol) of nonpolar compound B that is presented according to Example 1a is dissolved in 1.5 ml of tetrahydrofuran, mixed with 0.5 ml of water, 3 drops of a 4N hydrochloric acid and stirred under an atmosphere of argon for 16 hours at 23° C. It is poured into saturated sodium bicarbonate solution, extracted with diethyl ether, washed with saturated sodium chloride solution and dried on magnesium sulfate. The residue that is obtained after filtration and removal of solvent is purified by chromatography on an analytical thin-layer plate. A mixture of n-hexane and ethyl acetate is used as a mobile solvent; diethyl ether is used as an eluant. 4.2 mg (5.8 µmol, 29%) of the title compound is isolated as colorless foam, as well as 8.6 mg of starting material.

$^1$H-NMR (CDCl$_3$): δ=0.70 (3H), 0.80–1.08 (27H), 1.45 (9H), 2.31 (1H), 2.49 (1H), 2.54 (1H), 2.72 (1H), 2.86 (1H), 3.99 (1H), 4.54 (1H), 4.63 (1H), 5.08 (1H), 5.22–5.40 (3H), 5.75 (1H), 7.18–7.47 (9H) ppm.

EXAMPLE 9

[1R-[1α,2β(2R*,3S*),4α,4aβ,10aβ]]-3-[[(1,1-Dimethylethoxy)carbonyl]amino]-2-hydroxybenzenepropanoic acid-9-methylene-1,2,3,4,4a,9,10,10a-octahydro-1,11,11-trimethyl-4a,10a-dihydroxy-1,4-methanophenanthren-2-ylester 6.0 mg (8.3 µmol) of the compound that is presented according to Example 9a is reacted analogously to Example 1 and, after working-up and purification, 3.0 (5.3 µmol, 64%) of the title compound is isolated as colorless foam.

$^1$H-NMR (CDCl$_3$): δ=0.71 (3H), 1.04 (6H), 1.40 (9H), 2.22–2.48 (2H), 2.57 (1H), 2.73 (1H), 2.89 (1H), 3.01 (1H), 3.12 (1H), 3.95 (1H), 4.54 (1H), 5.12 (1H), 5.21 (2H), 5.37 (1H), 5.93 (1H), 7.22–7.50 (9H) ppm.

EXAMPLE 9a

[1R-[1α,2β(2R*,3S*),4α,4aβ,10aβ]]-3-[[(1,1-Dimethylethoxy)carbonyl]amino]-2-(triisopropylsilyloxy)benzenepropanoic acid-9-methylene-1,2,3,4,4a,9,10,10a-octahydro-1,11,11-trimethyl-4a,10a-dihydroxy-1,4-methanophenanthren-2-ylester 15 mg (21.4 µmol) of polar compound A that is presented according to Example 1a is reacted analogously to Example 8a and, after working-up and purification, 6 mg (8.3 µmol, 39%) of the title compound is isolated as colorless foam.

$^1$H-NMR (CDCl$_3$): δ=0.70 (3H), 0.78–1.50 (36H), 2.18–2.40 (2H), 2.56 (1H), 2.71 (1H), 2.86 (1H), 3.26 (1H), 4.25 (1H), 4.68 (1H), 5.12 (2H), 5.34 (2H), 5.99 (1H), 7.16–7.47 (9H) ppm.

EXAMPLE 10

[1R-[1α,2β(2R*,3S*),4α,4aβ,10aβ]]-3-[[Cyclohexylcarbonyl]amino]-2-hydroxybenzenepropanoic acid-9-methylene-1,2,3,4,4a,9,10,10a-octahydro-1,12,12-trimethyl-4a,10a-epoxy-1,4-methanophenanthren-2-ylester 38 mg (53 µmol) of the compound that is presented according to Example 10a is reacted analogously to Example 1 and, after working-up and purification, 24 mg (43 µmol, 81%) of the title compound is isolated as colorless foam.

$^1$H-NMR (CDCl$_3$): δ=0.60 (1H), 0.87 (3H), 0.93 (3H), 0.97–1.85 (14H), 2.22 (1H), 2.35 (1H), 2.76 (1H), 2.82 (1H), 3.10 (1H), 4.53 (1H), 5.08 (1H), 5.10 (1H), 5.47 (1H), 5.54 (1H), 7.19–7.45 (8H), 7.52 (1H), 7.58 (1H) ppm.

EXAMPLE 10a

[1R-[1α,2β(2R*,3S*),4α,4aβ,10aβ]]-3-[[Cyclohexylcarbonyl]amino]-2-(triisopropylsilyloxy)benzenepropanoic acid-9-methylene -1,2,3,4,4a,9,10,10a-octahydro-1,12,12-trimethyl-4a,10a-epoxy-1,4-methanophenanthren-2-ylester 15 mg (53 µmol) of compound A that is presented according to Example 1b and obtained enantiomer-free by crystallization as well as 34 mg of the β-lactam that is presented according to Example 1e are reacted analogously to Example 1a and, after working-up, 44 mg of the title compound is isolated as crude product, which is further reacted without purification.

¹H-NMR (CDCl₃): δ=0.70–1.85 (40H), 2.22 (2H), 2.66 (1H), 2.78 (1H), 3.07 (1H), 4.64 (1H), 5.01 (1H), 5.09 (1H), 5.47 (1H), 5.53 (1H), 7.10–7.41 (9H), 7.49 (1H), 7.56 (1H) ppm.

EXAMPLE 11

[1R-[1α,2β(2R*,3S*),4α,4aβ,10aβ]]-3-[Acetylamino]-2-hydroxybenzenepropanoic acid-9-methylene-1,2,3,4,4a,9,10,10a-octahydro-1,12,12-trimethyl-4a,10a-epoxy-1,4-methanophenanthren-2-ylester mg (μmol) of the compound that is presented according to Example 11a is reacted analogously to Example 1 and, after working-up and purification, mg (μmol, %) of the title compound is obtained as colorless foam.

¹H-NMR (CDCl₃): δ=0.86 (3H), 0.93 (3H), 1.08 (3H), 1.74 (1H), 1.97 (3H), 2.35 (1H), 2.77 (1H), 2.83 (1H), 2.97 (1H), 3.09 (1H), 4.48 (1H), 4.97 (1H), 4.99 (1H), 5.52 (1H), 5.56 (1H), 7.19–7.42 (7H), 7.56 (2H), 7.61 (1H) ppm.

EXAMPLE 11a

[1R-[1α,2β(2R*,3S*),4α,4aβ,10aβ]]-3-[Acetylamino]-2-(triisopropylsilyloxy)benzenepropanoic acid-9-methylene-1,2,3,4,4a,9,10,10a-octahydro-1,12,12-trimethyl-4a,10a-epoxy-1,4-methanophenanthrene-2-ylester 5.6 mg (20 μmol) of compound A that is presented according to Example 1b and is obtained enantiomer-free by crystallization as well as 22 mg of the β-lactam that is presented according to Example 1f are reacted analogously to Example 1a and, after working-up, 28 mg of the title compound is isolated as crude product, which is further reacted without purification.

¹H-NMR (CDCl₃): δ=0.81 (3H), 0.88 (3H), 0.95–1.30 (25H), 1.38 (1H), 1.98 (3H), 2.14 (1H), 2.65 (1H), 2.80 (1H), 3.08 (1H), 4.63 (1H), 4.93 (1H), 4.99 (1H), 5.50 (1H), 5.56 (1H), 7.15–7.38 (4H), 7.42–7.58 (4H), 7.67 (1H) ppm.

We claim:

1. Borneol derivatives of general formula I

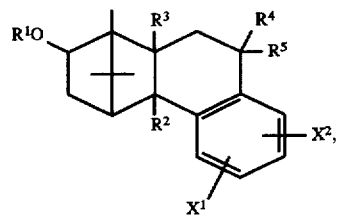

in which

R¹ means C(O)—CH(OR⁶)—CH(NHR⁷)—R⁸,

R² means hydrogen, —OH, $C_1$–$C_{10}$ alkyl, $C_1$–$C_{10}$ alkoxy, —OC(O)R⁹ᵃ, —OSO₂R⁹ᵃ, —OP(O)(OH)₂, NHR⁹ᵃ, NR⁹ᵃR⁹ᵇ, R³ means hydrogen, —OH, $C_1$–$C_{10}$ alkoxy, —OC(O)R⁹ᵇ, —OSO₂R⁹ᵇ, —OP(O)(OH)₂, or R², R³ together mean an oxygen atom, R⁴ means hydrogen, $C_1$–$C_{10}$ alkyl, —(CH₂)ₙ—OR¹¹ᵃ, R⁵ means hydrogen, $C_1$–$C_{10}$ alkyl, —(CH₂)ₚ—OR¹¹ᵇ, or R⁴, R⁵ together mean an oxygen atom, a =CHR¹⁰ group, n means 0 to 8, p means 1 to 8, R⁷ means —C(O)R¹², —SO₂R¹², —C(O)OR¹², —C(O)NHR⁹ᵈ, —C(O)NR⁹ᵈR⁹ᵉ,

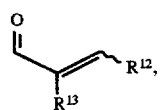

R⁸ means aryl,

R⁹ᵃ⁻ᵉ, R¹² are the same or different and mean $C_1$–$C_{10}$ alkyl, $C_4$–$C_8$ cycloalkyl, aryl, $C_7$–$C_{16}$ aralkyl, R¹⁰ means hydrogen, $C_1$–$C_{10}$ alkyl, —(CH₂)ₛ—OR¹⁴, s means 1 to 8, R⁶, R¹¹ᵃ·ᵇ, R¹⁴ are the same or different and mean hydrogen, $C_1$–$C_{10}$ alkyl, aryl, $C_7$–$C_{16}$ aralkyl, —SO₂R⁹ᶜ, —P(O)(OH)₂, R¹³, R¹⁵ᵃ·ᵇ are the same or different and mean hydrogen, $C_1$–$C_{10}$ alkyl, aryl, $C_7$–$C_{16}$ aralkyl, X¹, X² are the same or different and mean X, X can be hydrogen, halogen, —OH, —O₂, —N₃, —CN, —NR¹⁵ᵃR¹⁵ᵇ, —NHSO₂R¹⁵ᵃ, —CO₂R¹⁵, $C_1$–$C_{10}$ alkyl, $C_1$–$C_{10}$ alkoxy, $C_1$–$C_{10}$ acyloxy, $C_1$–$C_{10}$ acyl, or, if R¹⁵ means hydrogen, their salts with physiologically compatible bases.

2. Pharmaceutical agents that consist of one or more compounds of claim 1 and adjuvants, vehicles and additives that are commonly used, or their α-, β-, or γ-cyclodextrin clathrates, or the compounds of general formula I that are encapsulated with liposomes.

3. Process for the production of borneol derivatives of general formula I according to claim 1, which is characterized in that an olefin of general formula II

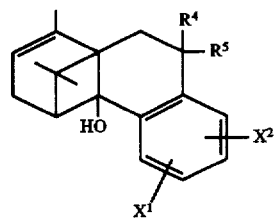

in which R⁴, R⁵, X¹ and X² have the above-mentioned meanings and are optionally protected in hydroxyl groups that contain X¹ or X², is epoxidated, and the epoxide formed is rearranged without isolation into an alcohol, of general formula III

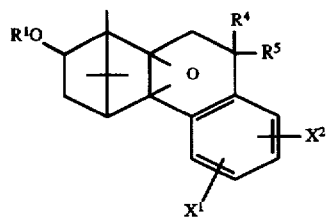

in which R⁴, R⁵, X¹ and X² have the above-mentioned meanings and hydroxyl groups that are contained in R¹, X¹ or X² are optionally protected, and this rearranged product is converted to a derivative of general formula I.

* * * * *